United States Patent [19]

Wolverton et al.

[11] Patent Number: 5,433,923
[45] Date of Patent: Jul. 18, 1995

[54] INDOOR HUMIDIFIER AND AIR PURIFIER

[76] Inventors: Billy C. Wolverton, 514 Pine Grove Rd.; John D. Wolverton, P.O. Box 411, both of Picayune, Miss. 39466

[21] Appl. No.: 150,225

[22] Filed: Nov. 10, 1993

Related U.S. Application Data

[63] Continuation-in-part of Ser. No. 832,479, Feb. 7, 1992, Pat. No. 5,217,696, and a continuation-in-part of Ser. No. 72,835, Jun. 7, 1993, Pat. No. 5,351,438.

[51] Int. Cl.⁶ ............................................. A62B 11/00
[52] U.S. Cl. ............................... 422/121; 47/59; 47/66; 47/79; 47/81; 422/5; 422/24; 422/122; 422/124; 422/171; 422/177; 422/211
[58] Field of Search ................... 422/120–122, 422/124, 123, 22, 171, 177, 211, 5, 24; 47/66 C, 79 I, 59, 79, 79 V, 81

[56] References Cited

U.S. PATENT DOCUMENTS

| | | | |
|---|---|---|---|
| 1,977,827 | 10/1934 | Kneller | 47/81 |
| 2,055,844 | 9/1936 | Kneller | 47/79 |
| 2,198,150 | 4/1940 | Barnhart | 47/62 |
| 2,387,340 | 10/1945 | Moriarty | 47/79 |
| 2,486,512 | 11/1949 | Armstrong | 47/79 X |
| 2,514,269 | 7/1950 | Wilberschied | 47/81 |
| 4,037,363 | 7/1977 | Baumann | 47/59 |
| 4,265,050 | 5/1981 | Buescher | 47/79 |
| 4,528,774 | 7/1985 | Skaife | 47/81 |
| 4,975,251 | 12/1990 | Saceman | 422/124 |
| 5,044,120 | 9/1991 | Couch | 47/79 |
| 5,130,091 | 7/1992 | Saceman | 422/124 X |
| 5,217,696 | 6/1993 | Wolverton et al. | 422/121 |
| 5,269,094 | 12/1993 | Wolverton et al. | 47/79 |
| 5,277,877 | 1/1994 | Jeffrey et al. | 422/124 |

OTHER PUBLICATIONS

Houseplants, Indoor Pollutants, and Allergic Reactions B. C. Wolverton, NASA Technology Labs, N.S.TL, MS 39529 Dec. 29, 1986.

*Primary Examiner*—Amalia L. Santiago

[57] ABSTRACT

A room humidifier and air purifier withdraws air from ambient room atmosphere into a region having a living plant with its roots in a growing media of highly adsorbent activated carbon and zeolite; passing air preferably downward through such media and back into the air over hot light bulbs which destroy undesirable airborne mold spores. The light bulbs are also used to supply sufficient light for plant growth and aesthetics through indirect lighting on the plant leaves.

14 Claims, 3 Drawing Sheets

INDOOR HUMIDIFIER AND AIR PURIFIER

RELATED APPLICATIONS

This Application is a continuation in part of Applicant's application Ser. No. 07/832,479 filed Feb. 7, 1992, now issued as U.S. Pat. No. 5,217,696, and application Ser. No. 08/072,835 filed Jun. 7, 1993, now U.S. Pat. No. 5,351,438.

BACKGROUND OF THE INVENTION

BACKGROUND

It is known that houseplants support complex biological and bacterial processes within the plant and also within the growth medium surrounding the plant roots, within which the plant is embedded, all of which tend to biodegrade various airborne pollutants, especially airborne hydrocarbons. This is summarized in Applicant's aforesaid patents.

The fact that low-light requiring houseplants culture microorganisms on and around their roots capable of destroying indoor air polluting chemicals have been demonstrated by B. C. Wolverton and John D. Wolverton (1993), "Plants and Soil Microorganisms: Removal of Formaldehyde, Xylene and Ammonia From The Indoor Environment," Journal of the Mississippi Academy of Science 38 (2) 11-15. The fact that certain houseplants can suppress levels of airborne microbes and add water vapor to rooms in which they are maintained has also been demonstrated by B. C. Wolverton and John D. Wolverton (1993) "Interior Plants: Their Influence On Airborne Microbes and Relative Humidity Levels Inside Energy-Efficient Buildings," Research Report No. WES/100/05-93/011; pp. 1-19; Plants for Clean Air Council, 10210 Bald Hill Road, Mitchellville, Md. 20721.

Prior art purification devices have been shown in U.S. Pat. No. 4,975,251 to Saceman in which a mechanical fan directs air into overlying soil in which certain plants grow to purify the air.

U.S. Pat. No. 4,786,812 to Humphries shows use of ultraviolet lamps to kill germs in moving air. The use of ultraviolet light as a bactericide has been widely known.

U.S. Pat. No. 4,845,602 to Lohecki shows a combined lamp and container apparatus.

A significant problem in regards to the use of plants and plant soil for purification of airborne contaminants is that the passage of air past the plant and especially through the plant's soil, tends to rapidly remove water, either by aspiration from the leaves of the plant or by evaporation from the soil particles. There is an optimum humidity for the soil in which a plant is embedded for best use as an air purifying medium; too much humidity blocks air flow and air purification, too little humidity results in the death of the plant.

There is also a known optimum humidity for human comfort. However, it has been discovered that maintaining a relatively high humidity from the point of comfort also significantly increases the incidence of airborne spores and bacterial contamination, which also propagate in higher humidity environments. In addition, various molds, fungi and other micro-organisms flourish under the humidity conditions that humans generally find most comfortable.

SUMMARY OF THE INVENTION

The invention is of a plant container particularly optimized for the purification of, and humidification of, the surrounding air in the room in which the plant is placed. The structure of the plant container is such that a reservoir of water is maintained within the plant container together a ready means of determining the level of the water within the reservoir. The plant growth medium is placed around the reservoir in such a manner as to provide for an optimum, continuous level of water seepage into the growth medium, so that the growth medium maintains an optimum moisture for growing the plant, but not such excessive moisture as to prevent the freeflow of air through the growth medium for the purposes of biological air purification.

The evaporative water gained in the passage of air through the soil during purification, combined with water aspiration by the plant maintains optimum comfort humidity levels within the room. The plant, being a living organism, varies its aspiration rate depending on the surrounding humidity and thus provides a form of closed cycle control to achieve but not exceed a desirable humidity level.

Further, it has been discovered that plant leaves appear to emit low levels of substances that suppress growth of airborne microbes in their immediate vicinity. These substances, which may include allelochemicales (forms of phenolic compounds) and terpenes, appear to be intended to reduce competition by other plants or to protect plants from harmful microbes, insects or animals. These chemicals emitted by houseplants appear to be an important factor in controlling the number and type of airborne microbes found in areas containing large numbers of plants; this appears to be related to evolved protective measures so that low light requiring houseplants, which typically have evolved in the humid environment underneath the canopy of a tropical rainforest, protect themselves from being overwhelmed by molds and microbes in such a humid environment.

Tests of the invention have shown that airborne microbial levels in a sunroom, in which 33% of the surface area is covered with fifteen different species of houseplants, were significantly lower than a control room without plants. Although humidity levels were 21% higher in the sunroom than in the control room, airborne microbial levels were 65% lower in the humid sunroom environment. Evapotranspiration rates of areca palm, Boston fern, chrysanthemum and dieffenbachia have been measured in a home and an office environment over a three month period. A large areca palm added approximately 656 ml of moisture per 24-hour period to a home environment. The Boston fern added 385 ml; the chrysanthemum 136 ml, and the dieffenbachia 61 ml of moisture to an office environment during 24 hours. While the rate of moisture will depend upon the plant specimen, size, temperature and relative humidity levels within in the room, the data demonstrates the potential use for certain house and office plants for adding mineral-free and microbial-free moisture to indoor environments to elevate humidity levels.

In general, the objectives of this invention are accomplished by withdrawing air from ambient room atmosphere into a region having a living plant with its roots in a growing media of highly absorbent activated carbon and zeolite; passing air preferably downward through such media and back into the air over hot light bulbs which destroy undesirable airborne mold spores. The light bulbs are also used to supply sufficient light for plant growth and aesthetics through indirect lighting on the plant leaves.

A primary objective of the present invention is to humidify room air by a combination of steps that are easy to understand, simple to carry out, but require complex biological reactions.

A further objective of this invention is to supply aesthetic indirect lighting which will allow the living plant to grow in areas containing low light levels. A further objective of this invention is to remove airborne microbes from the humid, purified air as it is moved past a hot light bulb by means of a fan.

Other objectives of this invention are to provide a large water reservoir and highly absorbent wicks to rapidly transfer moisture from the water reservoir to the plant roots where moisture is pumped into the room.

BRIEF DESCRIPTION OF THE FIGURES

FIG. 7 is an isometric view of the container of the invention.

DETAILED DESCRIPTION OF THE INVENTION

Figure 1:
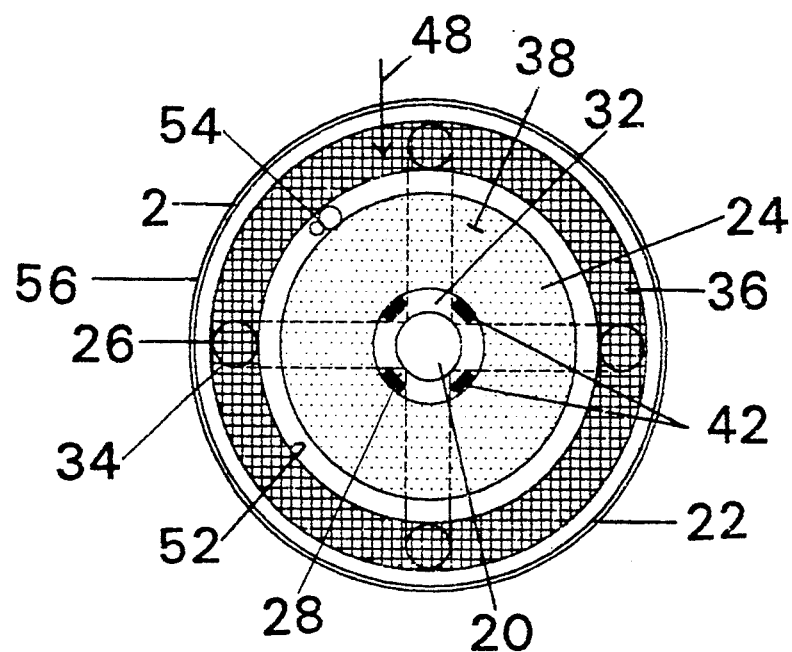
FIG. 1 is a horizontal cross-section view through the expanded clay and water reservoir level of one embodiment of the invention.
Figure 2:
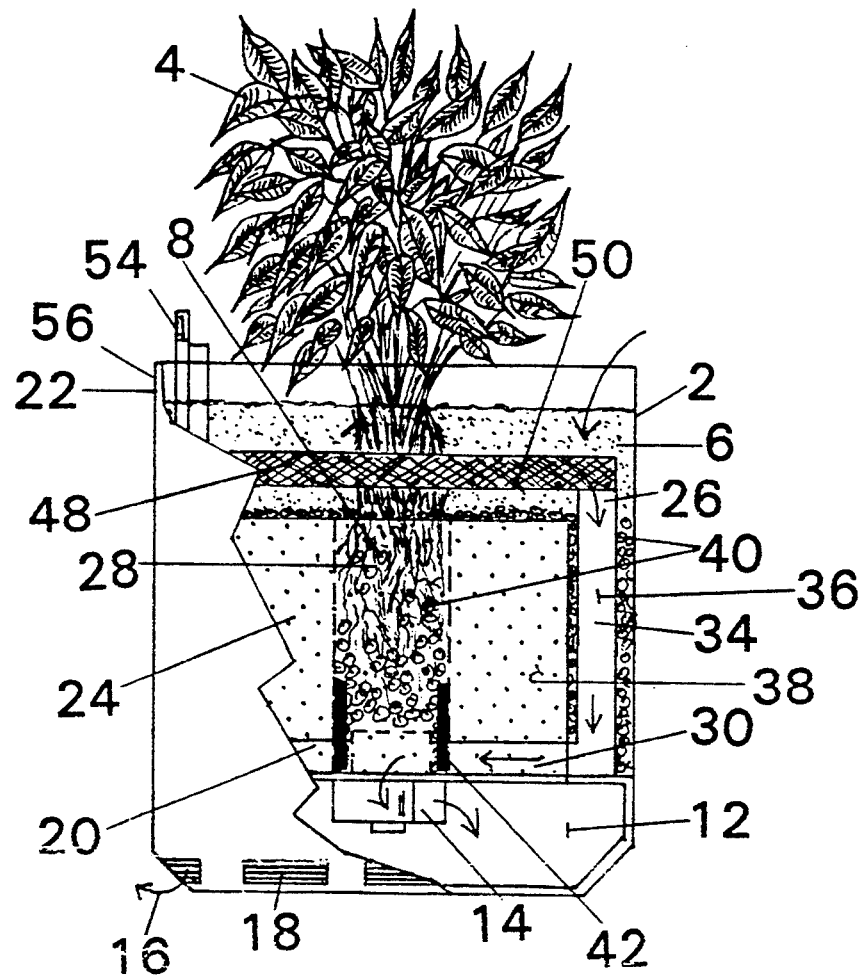
FIG. 2 is a cross-section side view of an embodiment of the invention.
Figure 3:
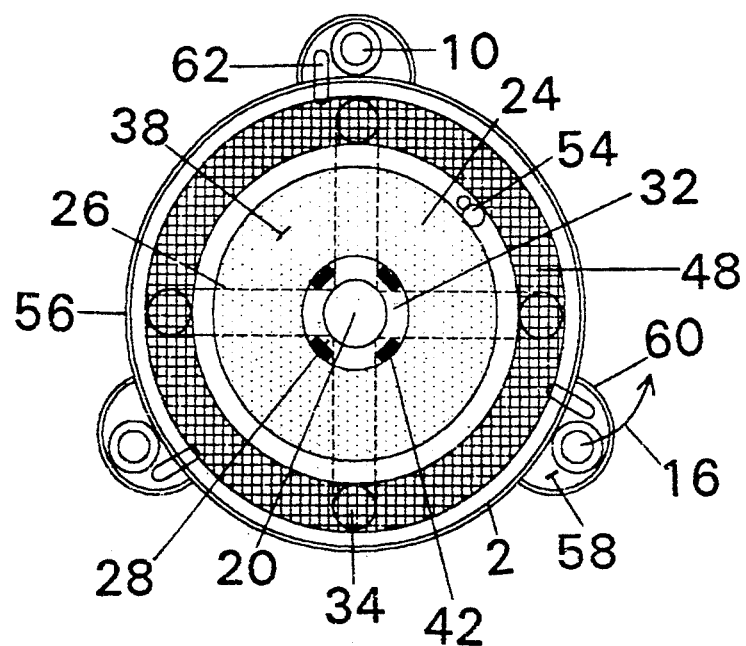
FIG. 3 is a horizontal cross-section view of a second embodiment of the invention.
Figure 4:
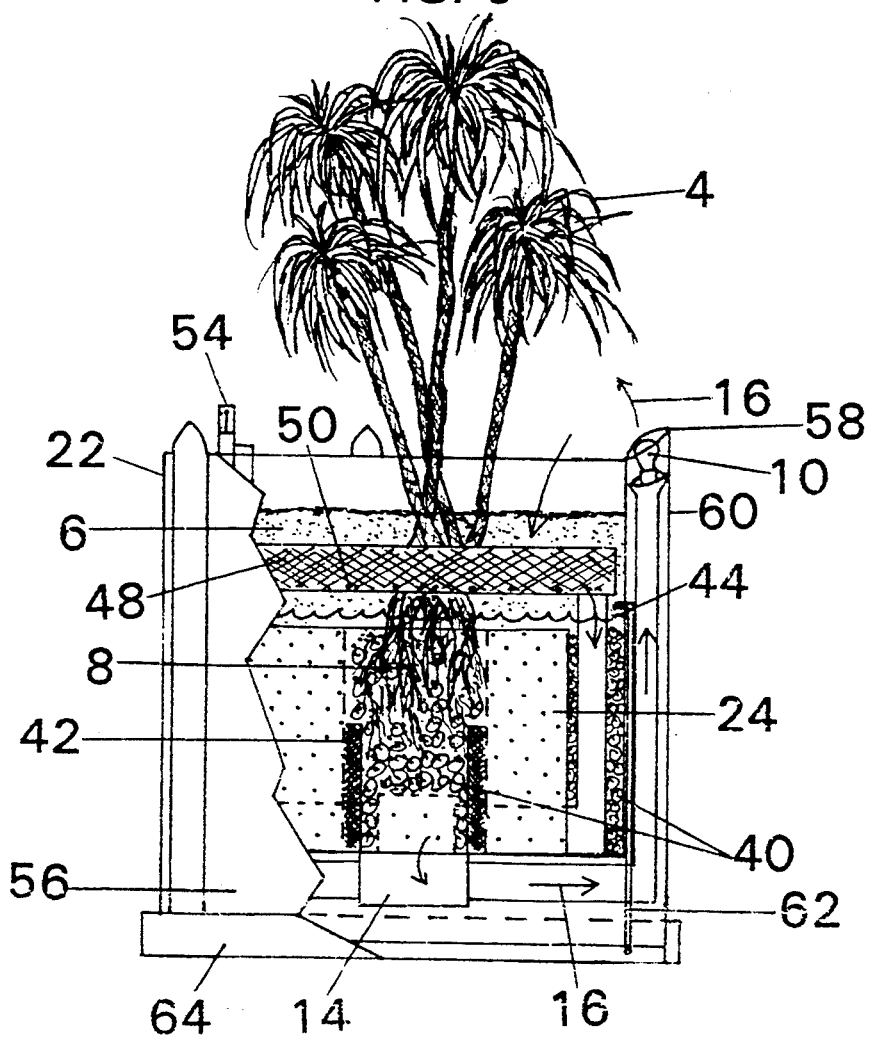
FIG. 4 is a cross-section side view of a second embodiment of the invention.

This invention, as shown in the Figures, is a container 2 for a growing houseplant 4 with a specific arrangement of the interior growing medium therein to provide a unitary air purifier and humidifier. The humidifier functions by withdrawing air from the ambient room atmosphere, through a growth medium 6 within the plant container 2. The arrows shown in the Figures show the air flow through the container. A houseplant 4 has roots 8 in the growth medium 6, which preferably comprises highly adsordent activated carbon and zeolite. The air is preferably drawn downward through this growth medium 6 and then blown back into the air over a hot light bulb 10 (shown in FIG. 2) to destroy undesirable airborne mold spores. The light bulbs 10 may also supply sufficient light for plant growth and/or for aesthetics through indirect lighting of the plant leaves.

Turning to the figures, the container 2 is shown as having a bottom clean air outlet chamber 12 within which is placed a fan 14, electrically motor driven and controlled by a timer. The fan 14 draws air from the region of the growth medium 6 into the bottom clean air chamber 12. This clean air 16 may be blown out from the container 2 through louvers 18 or returned through clean air ducts 20.

Above the clean air chamber 12 is a growth pot 22. This pot 22 is a sealed pot containing a water reservoir 24, growth media 6, and air flow ducting 26. A central axial region or chamber 28 extends downward through the water reservoir 24. The exhaust fan 14 passes through the bottom 30 of the growth pot 22, to provide air flow into the clean air chamber 12, but the growth pot 22 is otherwise sealed against any seepage into the clean air chamber 12.

An air flow duct 26, connected for air flow to the fan 14, rises and is preferably split into a plurality (four are shown) of transverse air ducts 32 extending outward through the water reservoir 24 and connected for air flow, each to a vertical air duct 234, all of which extend upward periodically around the inner-perimeter 36 of the pot 22.

Approximately the lower half to two-thirds of the plant growth pot 22 comprises the water reservoir 24. In the embodiments shown, this reservoir 24 is an annular chamber 38 around the central axial region 28. Within the inner perimeter 36 of the pot 22, which is outside of the annular water reservoir chamber 38, and within the central axial chamber 28, extending down within the water reservoir 24, is disposed a layer of expanded clay 40. Inside the annular water reservoir chamber 38 is an empty region filled only with liquid water. Openings in the walls of the chamber 38 pass water into the expanded clay 40. Within the central chamber 28 may be provided absorbent wicks 42 extending vertically up through the expanded clay 40 to above the level 44 of the water.

The water reservoir 24 need not have a water chamber 38; it may comprise simply a layer of expanded clay 40 or a similar saturated material. However, chamber 38 permits more water to be stored in a given size pot 22, decreasing the frequency with which water must be added to the pot 22.

Above the expanded clay 40, occupying approximately one-third to one-half of the vertical area of the pot 22, is a mixture 6 of activated carbon and zeolite which forms the growth medium 6 for a living houseplant 4. This houseplant 4 is chosen to have enhanced abilities to remove organic contaminants from the air. Typical such houseplants 4 include: weeping fig (*Ficus benjamina*), peace lily (*Spathiphyllum sp.*), areca palm (*Chrysalidocarpus lutescens*), corn plant (*Dracaena fragrans* "Massangeana"), lady palm (*Rhapis excelsa*), warneckei (*Dracaena deremensis* "Warneckei"), dumb cane (Dieffenbachia "*Exotica compacta*"), Ficus alli' (*Ficus alli'*), dumb cane (*Dieffenbachia camille*), elephant ear philodendron (*Philodendron domesticum*), golden pathos (*Epipremnum aureum*), arrowhead vine (*Syngonium podophyllum*), snake plant (*Sansevieria trifasciata* "Laurentii"), croton (*Codiaeum variegatum*) and umbrella grass (*Cyperus alternifolius*) and other known or discovered to have special efficiency for this purpose. Any plant will have some beneficial effect.

Each of the vertical air ducts 34 terminates in a closed horizontal annular duct or air intake 48 which is buried within the activated carbon and zeolite mixture 6 above the water reservoir 24. The air intake 48 in this embodiment is a closed tubular structure 46 connected for air flow to the vertical ducts 34, and having periodically spaced small apertures 50 or holes in its wall 52 for drawing air from the growth medium 6. Activation of fan 14 produces a low pressure within air intake 48, and this low pressure draws air in through the growth medium 6.

A vertical water fill indicator 54 is provided at one point along the inner-perimeter 36 of the pot 22. This indicator 54 may be of the type shown in our co-pending patents, or any vertical tubular structure extending down into the water reservoir 24 which is capable of remotely indicating the level of water 44 within the pot 22.

Optionally, at spaced intervals around the outer side 56 of the pot, are provided sources of radiant energy 58 which preferably are aimed so as to illuminate the underside of the leaves of the plant. Each such source 58 is located within a vertically extending clean air duct 60 which extends vertically down the outer side 56 of the pot and is connected for air flow to the clean air chamber 12 in the underside of the pot 22. The interconnection between the air intake 48, the interior air flow ducting 26, the exhaust fan 14, the clean air chamber 12 and the clean air vertical exhaust ducts 60 is sealed to assure positive air flow from the growth medium 6 to the outside air.

Also, optionally, a drain pipe 62 may be provided at a desired maximum reservoir water level 44, the pipe 62 extending from within the pot 22 through an opening in the sidewall 56 of the pot, draining down into an overflow tray 64 placed beneath an exterior to the overall container 2. This overflow pipe 62 establishes the maximum water level 44 within the expanded clay 40 and is a second positive indication of over-watering.

In use, the assembled container 2 is filled with water to a level 44 defining that of the water reservoir 24. The water reservoir 24, occupying a substantial part of the volume of the pot 22, holds a relatively large amount of water. This amount of water is significantly increased by the annular chamber 38. The water communicates, via the vertical absorbent wicks 42, within the central chamber 28 and holes in the chamber 38 walls into the expanded clay fill 40 saturating the expanded clay 40. Any material which saturates readily in contact with water may, of course, be used instead of expanded clay 40. Expanded clay 40 is chosen due to its excellent capillary flow properties with water. The water essentially wicks itself uniformly throughout the expanded clay fill 40.

From this point water flow is by a combination of wicking and capillary flow, uniformly through the activated carbon and zeolite mixture 6. The differential wetting properties of the expanded clay 40, in contrast to the carbon and zeolite mixture 6, are such that whereas the expanded clay 40 remains saturated so long as any water remains in the reservoir 24, the carbon and zeolite mixture 6 is moistened but not saturated. It remains permeable to air flow, but sufficiently moist to support bacteriological action.

The roots 8 of the houseplant 4 extend down through the activated carbon and zeolite mixture 6 and into the expanded clay 40 within the water reservoir 24. Since the root structure 8 is in both the activated carbon and zeolite mixture 6 and in the expanded clay mixture 40 the plant 4 will naturally expand or retract its roots 8 to achieve an optimum water level at the roots 8 depending upon the specific species of plant 4. Those plants 4 which require less water will tend to grow more aggressively within the carbon and zeolite mixture 6; those plants 4 which require a more saturated environment will extend downward into the activated expanded clay 40.

It has been discovered that despite the stratification of the carbon and zeolite mixture 6 above the expanded clay 40, and the differential water saturation between both, that the beneficial pollution absorbing microbes associated with the roots of the houseplant 4 will migrate into the activated carbon and zeolite 6 mixture, coating the moistened but not fully wet particles. In turn, the activated carbon and zeolite mixture 6 remains porus and permeable to air flow.

Activation of the electric fan 14 pulls a low air pressure within the air intake 48 within the carbon and zeolite mixture 6, pulling air into the air intake 48 and thus drawing it through the biologically active carbon and zeolite mixture 6. The microbes within the mixture, being in a moist and therefore active state, remove organic contaminants from the air. As these microorganisms die or are consumed, they are replenished in turn by additional microbes growing within the root structure 8 of the houseplant. The air drawn into the air intake 48 therefore has biologically reduced levels of organic air pollutants.

At the same time the air has been humidified by being drawn through the moist carbon and zeolite mixture 6. The water removed by this humidification process is readily replenished from the relatively large quantity of water within the water reservoir 22, which percolates through the expanded clay 40, into the carbon and zeolite mixture 6, maintaining the relative humidity levels of each.

In a first embodiment of the invention, the clean air 16 is emitted from the exhaust fan 14 through the clean air chamber louvers 18 and out into the room. In a second embodiment of the invention, the humidified and purified air is blown by the exhaust fan 14 through the vertical clean air ducts 60, past the source of radiant energy 58. It is preferable that these sources of radiant energy 58 be illuminating lights 10, preferably lights 10 having a bactericidal property, as well as a growth enhancing property with the plant 4. This can be provided by lights 10 having some ultra-violet output, but preferably the lights 10 have a significant thermal output, so that a heated region around each lightbulb 10 serves to significantly reduce any residual microbes, spaces or other microorganisms which may still have been picked up within the moist, humid environment of the plant's growth media 6.

Figure 5:
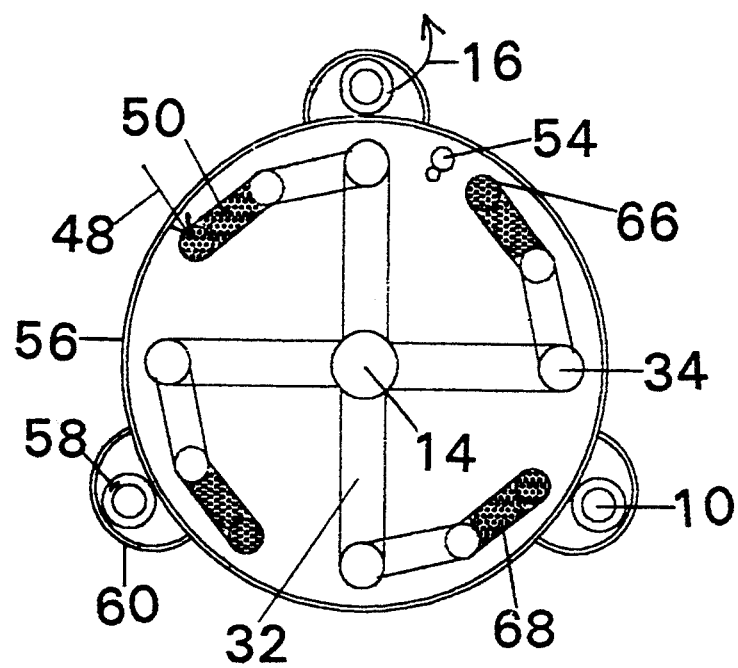
FIG. 5 is a top view of the invention showing a second embodiment of the air inlet.
Figure 6:
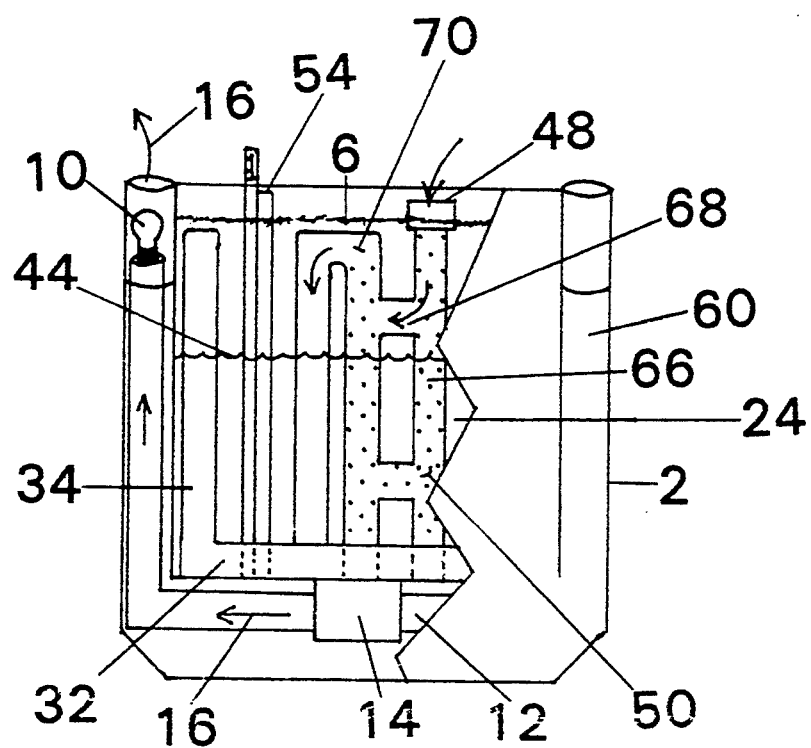
FIG. 6 is a side section view of the invention showing a second embodiment of an air inlet.

FIGS. 5 and 6 show yet another embodiment of the invention. In this embodiment, a plurality of air intakes 48 of the invention each comprises a plurality of vertical perforated adjacent tubes 66, each parallel to one another along the inner perimeter 36 of the pot 22. The vertical perforated tubes 66 extend from just at the upper level of the growth media 6, down through the expanded clay 40 into the water reservoir 24. Each of the vertically perforated tubes 66 within an individual air intake 48 is connected at a plurality of levels by horizontal cross tubes 68. One of the perforated tubes 66 connects at an upper end 70 within the pot 22 to one of the vertically extending air inlet ducts 34. An independent set of vertically extending air intakes 48 exists for each vertical air inlet duct 34.

In use the perforated tubes 66 extend vertically down through the growth media 6, below the water level 44. That portion of the perforated tubes 66 below the water level 44 will, of course, be filled with water. At least one of the horizontal cross tubes 68 is placed so as to always be above the water level 44; other of the horizontal cross tubes 68 are placed at levels corresponding to stages of decrease in water level 44 as the water within the water reservoir 24 is exhausted due to evaporation or plant growth.

The fan 14, pulling a suction through the air flow ducting 26, and through each of the air inlet tubes 66, pulls air from the top 70 of one of the perforated inlet tubes 66. Since at least one horizontal cross tube 68 interconnects all the perforated tubes 66 of an air inlet 48, air is drawn from that portion of the air intake tube 66 which is above the water level 44, but embedded in the growth media 6 and or the expanded clay 40. This provides for a more uniform intake of air through all of the growth media 6 which is not saturated with water. That portion of the air intake 48 below the saturated water level 44 is filled with water, which can directly evaporate into the inlet air, aiding in humidification. The construction of the air inlet 48 with at least one cross tube 68 above the water level 44 at all times, and with the air being drawn off the top 70 of the air inlet 66, prevents any water from being drawn into the clean air chamber 12 at all water levels 44 within an upper to a lower water level within the reservoir 24.

As with the other embodiments, all the cleaned humidified air is drawn through a single fan 14 into an air chamber 12 beneath the plant pot 22, and emitted through an air outlet 18, 60. The outlets preferably are independent air ducts 60, each containing a light 10 at the upper end of the air duct 60. The light 10 is preferably an incandescent bulb or a growth lamp shining upward onto the plant 4. The light's 10 radiation emission, a combination of heat, emitted by a incandescent bulb 10, or any ultraviolet light as may be emitted by the growth lamp 10, serves to significantly reduce any residual microbes or spores emitted in the cleaned and humidified air 16. Further, the humidified cleaned air 16 passes generally through the leaf region of the plant 4 providing for further treatment of the air in terms of exposing the clean air 16 to the antimicrobial emissions from the leaves of the plant 4.

It has been determined that the normal growth process of the plant 4 tends to suppress microbes other than those intimately associated with the plant's own root system, existing in symbiotic relationship with this plant. The radiant energy 58 light tends to eliminate any spread of these remaining microorganisms which may be picked up in the clean air flow 16, so that the invention reduces microbe level in the air by a combination of biological processes associated with the plant and by thermally heating the clean air after it has been humidified and passed through the plant growth medium.

The resulting invention provides a continuing balanced humidity level so long as water remains in the reservoir 24. The water fill indicator 54 therefore serves to indicate either too much or too little water, indicating the need for refilling the reservoir 24. The optional overflow pipe 62 prevents any excessive water level, which would tend to flood the carbon and zeolite mixture 6 and shut off air flow to the air intake 48. So long as water remains in the reservoir 24, an essentially uniform percentage of water will be present throughout the carbon and zeolite mixture 6. This constant water level serves to humidify the air, both directly by evaporation as air is drawn through the carbon and zeolite mixture 6, and by transpiration from the plant 4 leaves into the atmosphere. The negative effects of such humidity, an increase in fungi and microorganisms, is avoided by the combination of the plant's own ability to suppress the growth of microorganisms and, additionally, by the optional radiant energy lights 58 placed within the clean air outlets 60. The end result is that the invention disclosed provides both a uniform, comfortable level of humidity within a closed room, and significantly reduces the presence of organic contaminants and micro organisms within the air in the room. The device therefore is a particularly useful combined air purifier and air humidifier using natural, biological processes, which are both renewable and self-sustainable.

I claim:
1. An apparatus for purifying and humidifying air within a confined space comprising:
   a container for containing a living plant, said container defining a root zone therewithin for the growth of root;
   a water reservoir defined within said container;
   an air permeable growth media within said container separate from, but connected to, said water reservoir for capillary water flow therefrom, said media being unsaturated with water;
   means for drawing air into and through said growth media and for expelling said air into a confined space surrounding said container; and
   an area of expanded clay, inside said container beneath said growth media.

2. The apparatus of claim 1 said water reservoir further comprising:
   an area of expanded clay, filling said container beneath said growth medium.

3. The apparatus of claim 1, said water reservoir further comprising:
   an open annular water chamber within said container;
   said annular water chamber surrounding a central axial zone within said container;
   said annular water chamber being spaced a distance from the sidewalls of said container; said area of expanded clay filling said central axial area and
   a layer of expanded clay surrounding said annular water chamber;
   and means for conducting water reservoir from said reservoir into said expanded clay area.

4. The apparatus of claim 3, said means for conducting water further comprising:
   a plurality of vertical wicks extending within said central axial area from within said expanded clay in said central axial area up to within said growth media.

5. The apparatus of claim 1, said means for drawing and expelling air further comprising:
   a horizontally disposed toroidal air inlet, having air flow perforations, disposed within said growth media;
   a plurality of ducts extended for air flow from said air inlet to an exhaust fan within said container;
   said exhaust fan exhausting air through a clean air outlet of said container.

6. The apparatus of claim 1, wherein said means for drawing and expelling air comprise:
   at least one set of a plurality of perforated tubes extending from within the said water reservoir up to within said growth media;
   at least one perforated horizontal tube interconnecting a respective of said vertical perforated tubes; an exhaust fan
   means connecting the top of at least one of said vertical perforated tubes, for air flow, with an inlet to said an exhaust fan;
   said exhaust fan drawing air from said perforated tube, expelling said air from a clean air outlet of said exhaust fan.

7. The apparatus of claim 5 wherein said clean air outlet is a plurality of louvers located around a base of said container.

8. The apparatus of claim 6 wherein said clean air outlet is a plurality of louvers located within a base of said container.

9. The apparatus of claim;1, said means for drawing and expelling air further comprises:
- a plurality of a clean air outlets, each comprising a duct extending up the outside of said apparatus;
- means within each said duct for applying radiant energy into air flowing out of said clean air outlet;
- said radiant energy decreasing the microbe and spore content of clean air emitted from said duct.

10. The apparatus of claim 9, said means for applying radiant energy comprising:
- a growth lamp within the outlet of each said duct, said growth lamp illuminating the base of a plant within said container.

11. The apparatus of claim 9, said means for applying radiant energy comprising:
- an incandescent lamp within each clean air duct, said incandescent lamp illuminating the base of a plant within said container.

12. The apparatus of claim 9, said means for applying radiant energy comprising:
- an ultraviolet light source within each duct.

13. The apparatus of claim 5, said means for expelling air comprise:
- a plurality of clean air outlets, each comprising a duct extending up the outside of said apparatus;
- means within each said duct for imposing radiant energy into air flowing out of said clean air outlet;
- said radiant energy decreasing the microbe and spore content of clean air emitted from said duct.

14. The apparatus of claim 6, said means for expelling air further comprises:
- a plurality of clean air outlets, each comprising a duct extending up the outside of said apparatus;
- means within each said duct for imposing radiant energy into air flowing out of said clean air outlet;
- said radiant energy decreasing the microbe and spore content of clean air emitted from said duct.

* * * * *